US012611145B2

(12) United States Patent
Rafiei et al.

(10) Patent No.: US 12,611,145 B2
(45) Date of Patent: Apr. 28, 2026

(54) SEVERITY ESTIMATION SYSTEM FOR OCCUPANTS IN A VEHICLE

(71) Applicant: GM Global Technology Operations LLC, Detroit, MI (US)

(72) Inventors: Ali Rafiei, Newmarket (CA); Chin-Hsu Lin, Troy, MI (US); Alaa M. Khamis, Courtice (CA); Alok Warey, Novi, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 255 days.

(21) Appl. No.: 18/503,695

(22) Filed: Nov. 7, 2023

(65) Prior Publication Data

US 2025/0143645 A1     May 8, 2025

(51) Int. Cl.
*G06K 9/00*        (2022.01)
*A61B 5/00*        (2006.01)
        (Continued)

(52) U.S. Cl.
CPC .......... *A61B 5/6893* (2013.01); *A61B 5/0077* (2013.01); *A61B 5/01* (2013.01); *A61B 5/05* (2013.01); *B60R 21/0132* (2013.01); *B60R 21/01542* (2014.10); *E05B 77/02* (2013.01); *E05F 15/72* (2015.01); *G06V 10/803* (2022.01); *G06V 20/59* (2022.01); *G10L 25/51* (2013.01); *E05Y 2900/55* (2013.01)

(58) Field of Classification Search
CPC ...... G06V 10/803; G06V 20/59; G06V 20/56; G06V 20/58; G10L 25/51; G06T 2207/30248; G06T 2207/30252; A61B 5/6893; A61B 5/0077; A61B 5/01; A61B 5/05; B60R 21/01542; B60R 21/0132; E05F 15/72; E05B 77/02; E05Y 2900/55
See application file for complete search history.

(56) References Cited

U.S. PATENT DOCUMENTS 9,646,428 B1     5/2017  Konrardy et al.
11,518,330 B2 *  12/2022  Park ....................... G06V 20/58
                    (Continued)

FOREIGN PATENT DOCUMENTS

DE          102017103969 A1     8/2017

*Primary Examiner* — Avinash Yentrapati

(74) *Attorney, Agent, or Firm* — Vivacqua Crane, PLLC

(57)                ABSTRACT

A severity estimation system for one or more occupants located in an interior cabin of a vehicle involved in a vehicle-related incident includes one or more microphones located within the interior cabin of the vehicle that capture audio-based inputs, an occupant monitoring system (OMS) that collects scene recognition inputs indicative of a status of the occupants, a restraint system that collects a plurality of restraint-based inputs indicative of one or more restraint-based mechanisms associated with an occupant of the vehicle being activated during the vehicle-related incident, a motion-based indicator system that collect the plurality of motion-based inputs indicative of the motion of the vehicle during the vehicle-related incident, and one or more controllers. The one or more controllers fuse together the audio-based indicator, the OMS indicator, the restraint-based indicator, and the motion-based indicator to determine an incident severity indicator corresponding to the one or more occupants.

18 Claims, 5 Drawing Sheets

(51) Int. Cl.

| | |
|---|---|
| *A61B 5/01* | (2006.01) |
| *A61B 5/05* | (2021.01) |
| *B60R 21/0132* | (2006.01) |
| *B60R 21/015* | (2006.01) |
| *E05B 77/02* | (2014.01) |
| *E05F 15/72* | (2015.01) |
| *G06V 10/80* | (2022.01) |
| *G06V 20/59* | (2022.01) |
| *G10L 25/51* | (2013.01) |

(56) References Cited

U.S. PATENT DOCUMENTS

| | | | |
|---|---|---|---|
| 12,246,708 B2 * | 3/2025 | Nave | G08B 25/006 |
| 2004/0148188 A1 | 7/2004 | Uegaki | |
| 2007/0203866 A1 | 8/2007 | Kidd et al. | |
| 2012/0146766 A1 * | 6/2012 | Geisler | G07C 5/085 |
| | | | 340/8.1 |
| 2015/0035665 A1 * | 2/2015 | Plante | G07C 5/085 |
| | | | 340/438 |
| 2019/0279447 A1 | 9/2019 | Ricci | |
| 2019/0370576 A1 | 12/2019 | Surendran et al. | |
| 2020/0372727 A1 | 11/2020 | Sudhir et al. | |
| 2023/0154308 A1 * | 5/2023 | Nave | G06F 30/20 |
| | | | 340/539.13 |
| 2023/0256903 A1 | 8/2023 | Gilbert-Eyres et al. | |
| 2023/0316784 A1 | 10/2023 | Damodharan | |
| 2024/0059323 A1 | 2/2024 | Gerrese et al. | |
| 2025/0143645 A1 | 5/2025 | Rafiei et al. | |
| 2025/0148840 A1 | 5/2025 | Khamis et al. | |

* cited by examiner

50

| A1 | A2 | | | |
|---|---|---|---|---|
|  |  | F | U | T |
|  | F | F | U | T |
|  | U | U | U | T |
|  | T | T | T | T |

52

| S1 |  | S2 | | |
|---|---|---|---|---|
|  |  | F | U | T |
|  | F | F | F | F |
|  | U | F | U | U |
|  | T | F | U | T |

SEVERITY ESTIMATION SYSTEM FOR OCCUPANTS IN A VEHICLE

INTRODUCTION

The present disclosure relates to a severity estimation system for estimating an incident severity indicator corresponding to one or more occupants in a vehicle involved in a vehicle-related incident. The severity estimation system also selects one or more remedial actions to perform based on the incident severity indicator.

There are various remedial actions that may be performed after a vehicle undergoes a vehicle-related incident, such as a collision, that assist the occupants of a vehicle. For example, if the vehicle is involved in a relatively minor collision that does not affect the occupants, then non-emergency personnel may be contacted by a subscription-based vehicle communication system. In contrast, if the collision is more severe, then emergency personnel may be contacted in addition to the non-emergency personnel. In some situations, the doors are unlocked, or the windows are lowered after the vehicle undergoes a vehicle-related incident.

It is to be appreciated that some types of remedial actions may be more appropriate or helpful when compared to some other types of remedial actions that are performed after a vehicle undergoes a vehicle-related incident, depending upon the specific details as well as the severity of the collision. For example, it may not be particularly helpful or necessary to contact emergency personnel for a relatively minor collision. As another example, in some situations it might be helpful to lower the windows or unlock the doors of the vehicle when the vehicle is in a body of water, depending upon the water level. As another example, it may be especially helpful to unlock the doors of the vehicle, such as when smoke is present within the interior cabin.

Thus, while current vehicle-related incident response systems achieve their intended purpose, there is a need in the art for an improved approach for determining remedial actions that may be performed after a vehicle undergoes a collision.

SUMMARY

According to several aspects, a severity estimation system for one or more occupants located in an interior cabin of a vehicle involved in a vehicle-related incident is disclosed. The severity estimation system includes one or more microphones located within the interior cabin of the vehicle that capture a plurality of audio-based inputs indicative of verbal and non-verbal sounds emitted by the one or more occupants of the vehicle, an occupant monitoring system (OMS) that collects a plurality of scene recognition inputs indicative of a status of the occupants, a restraint system that collects a plurality of restraint-based inputs indicative of one or more restraint-based mechanisms associated with an occupant of the vehicle being activated during the vehicle-related incident, a motion-based indicator system that collect a plurality of motion-based inputs indicative of the motion of the vehicle during the vehicle-related incident, and one or more controllers in electronic communication with the one or more microphones, the OMS, the restraint system, and the motion-based indicator system. The one or more controllers execute instructions to combine the plurality of audio-based inputs based on at least a 2-value logic system to determine an audio-based indicator, the plurality of scene recognition inputs based on the at least 2-value logic system to determine an OMS indicator, and the plurality of restraint-based inputs based on the at least 2-value logic system to determine a restraint-based indicator. The one or more controllers combine the plurality of motion-based inputs from the motion-based indicator system based on a weighted sum model to determine a motion-based indicator. The one or more controllers fuse together the audio-based indicator, the OMS indicator, the restraint-based indicator, and the motion-based indicator to determine an incident severity indicator corresponding to the one or more occupants, where the incident severity indicator is a numerical value representative of a level of severity of an effect the vehicle-related incident has upon the one or more occupants.

In another aspect, the one or more controllers execute instructions to fuse together the audio-based indicator, the OMS indicator, the restraint-based indicator, and the motion-based indicator based on a weighted formula to determine the incident severity indicator.

In yet another aspect, the weighted formula is expressed as:

$$Y = W_A I_{audio} + W_M I_{motion} + W_O I_{OMS} + W_R I_{Res}$$

where $W_A$ is a weight corresponding to the audio-based indicator $I_{audio}$, $W_M$ is a weight corresponding to the motion-based indicator $I_{motion}$, $W_O$ is a weight corresponding to the OMS indicator $I_{OMS}$, and $W_R$ is a weight corresponding to the restraint-based indicator $I_{Res}$.

In an aspect, the one or more controllers execute instructions to select one or more remedial actions based on the incident severity indicator, an unconsciousness probability indicator, and a root cause probability indicator.

In yet another aspect, the one or more remedial actions include one or more of the following: contacting emergency personnel, unlocking doors of the vehicle, lowering windows of the vehicle, sending an SOS signal to one or more vehicles that are located within a predefined radius from the vehicle, and contacting non-emergency personnel.

In an aspect, the 2-value logic system is one of a binary logic system and a ternary logic system.

In another aspect, the audio-based inputs are combined based on ternary OR-based logic.

In yet another aspect, the OMS includes one or more cameras positioned within the interior cabin of the vehicle to capture image data indicative of the one or more occupants.

In an aspect, the one or more cameras include one or more of the following: a red, green, and blue (RGB) camera that captures visible light image data, an infrared camera that captures infrared image data, and a thermal camera that captures thermal image data.

In another aspect, the OMS includes one or more of the following: one or more biometric sensors and one or more radar sensors.

In yet another aspect, the plurality of scene recognition inputs include one or more of the following: eye status inputs based on the eyes of the occupants, head status inputs based on the head of the occupants, vital status inputs, body velocity inputs, seat belt status inputs, seat belt speed inputs, contact inputs indicating contact between the occupants and an interior of the vehicle, and airbag inputs.

In an aspect, the plurality of motion-based inputs include one or more of the following: an acceleration and deceleration input, an impact angle input, a roll-over input, and a velocity change input.

In another aspect, the weighted sum model is expressed as:

$$I_{motion} = \omega_{M1} \times M1 + \omega_{M2} \times M2 + \omega_{M3} \times M3 + \omega_{M4} \times M4 = 1$$

where $\omega_{M1}$ represents a first weighting factor corresponding to the acceleration and deceleration input M1, $\omega_{M2}$ represents a second weighting factor corresponding to the impact angle input M2, $\omega_{M3}$ represents a third weighting factor corresponding to the roll-over input M3, and $\omega_{M1}$ represents a fourth weighting factor corresponding to the velocity change input M4.

In yet another aspect, the plurality of restraint-based inputs from the restraint system include one or more of the following: an anchor pretensioner input, a load limiter input, a first stage deployment input, and a dual stage deployment input.

In an aspect, the motion-based indicator system includes one or more of the following: a sensing and diagnostic module (SDM) and an electronic data recorder (EDM).

In another aspect, a severity estimation system for one or more occupants located in an interior cabin of a vehicle involved in a vehicle-related incident. The severity estimation system includes one or more microphones located within the interior cabin of the vehicle that capture a plurality of audio-based inputs indicative of verbal and non-verbal sounds emitted by the one or more occupants of the vehicle, an OMS that collects a plurality of scene recognition inputs indicative of a status of the occupants, a restraint system that collects a plurality of restraint-based inputs indicative of one or more restraint-based mechanisms associated with an occupant of the vehicle being activated during the vehicle-related incident, a motion-based indicator system that collect a plurality of motion-based inputs indicative of the motion of the vehicle during the vehicle-related incident, and one or more controllers in electronic communication with the one or more microphones, the OMS, the restraint system, and the motion-based indicator system. The one or more controllers execute instructions to combine the plurality of audio-based inputs based on at least a 2-value logic system to determine an audio-based indicator, the plurality of scene recognition inputs based on the at least 2-value logic system to determine an OMS indicator, and the plurality of restraint-based inputs based on the at least 2-value logic system to determine a restraint-based indicator. The one or more controllers combine the plurality of motion-based inputs from the motion-based indicator system based on a weighted sum model to determine a motion-based indicator. The one or more controllers fuse together the audio-based indicator, the OMS indicator, the restraint-based indicator, and the motion-based indicator based on a weighted formula to determine an incident severity indicator corresponding to the one or more occupants, where the incident severity indicator is a numerical value representative of a level of severity of an effect the vehicle-related incident has upon the one or more occupants.

In another aspect, the weighted formula is expressed as:

$$Y = W_A I_{audio} + W_M I_{motion} + W_O I_{OMS} + W_R I_{Res}$$

where $W_A$ is a weight corresponding to the audio-based indicator $I_{audio}$, $W_M$ is a weight corresponding to the motion-based indicator $I_{motion}$, $W_O$ is a weight corresponding to the OMS indicator $I_{OMS}$, and $W_R$ is a weight corresponding to the restraint-based indicator $I_{RES}$.

In yet another aspect, the one or more controllers execute instructions to select one or more remedial actions based on the incident severity indicator, an unconsciousness probability indicator, and a root cause probability indicator.

In an aspect, the one or more remedial actions include one or more of the following: contacting emergency personnel, unlocking doors of the vehicle, lowering windows of the vehicle, sending an SOS signal to one or more vehicles that are located within a predefined radius from the vehicle, and contacting non-emergency personnel.

In another aspect, a severity estimation system for one or more occupants located in an interior cabin of a vehicle involved in a vehicle-related incident. The severity estimation system includes one or more microphones located within the interior cabin of the vehicle that capture a plurality of audio-based inputs indicative of verbal and non-verbal sounds emitted by the one or more occupants of the vehicle, an OMS that collects a plurality of scene recognition inputs indicative of a status of the occupants, a restraint system that collects a plurality of restraint-based inputs indicative of one or more restraint-based mechanisms associated with an occupant of the vehicle being activated during the vehicle-related incident, a motion-based indicator system that collect a plurality of motion-based inputs indicative of the motion of the vehicle during the vehicle-related incident, and one or more controllers in electronic communication with the one or more microphones, the OMS, the restraint system, and the motion-based indicator system. The one or more controllers execute instructions to combine the plurality of audio-based inputs based on at least a 2-value logic system to determine an audio-based indicator, the plurality of scene recognition inputs based on the at least 2-value logic system to determine an OMS indicator, and the plurality of restraint-based inputs based on the at least 2-value logic system to determine a restraint-based indicator. The one or more controllers combine the plurality of motion-based inputs from the motion-based indicator system based on a weighted sum model to determine a motion-based indicator. The one or more controllers fuse together the audio-based indicator, the OMS indicator, the restraint-based indicator, and the motion-based indicator based on a weighted formula to determine an incident severity indicator corresponding to the one or more occupants, where the incident severity indicator is a numerical value representative of a level of severity of an effect the vehicle-related incident has upon the one or more occupants. The one or more controllers select one or more remedial actions based on the incident severity indicator, an unconsciousness probability indicator, and a root cause probability indicator.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
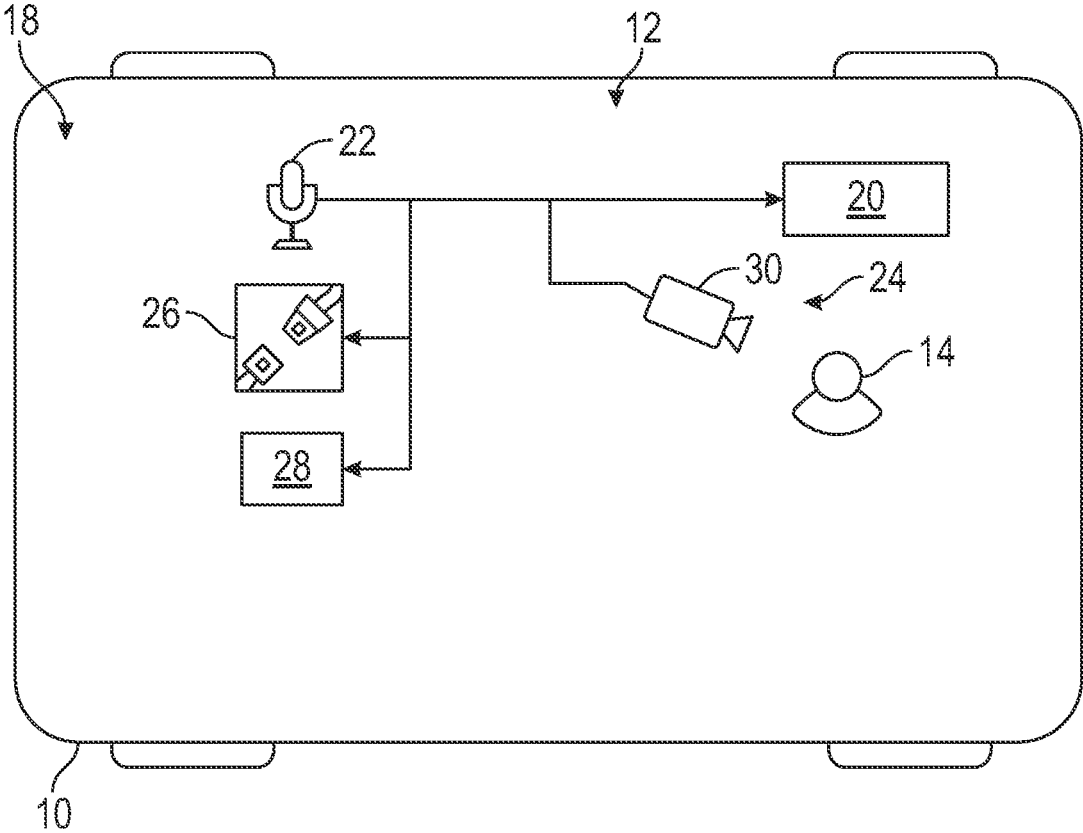
FIG. 1 illustrates a schematic diagram of vehicle including the disclosed severity estimation system including one or more controllers in electronic communication with a microphone, an occupant monitoring system (OMS), a restraint system, and a motion-based indicator system, according to an exemplary embodiment.

Referring to FIG. 1, a vehicle 10 including the disclosed severity estimation system 12 is illustrated. As explained below, the severity estimation system 12 employs a multi-modal approach for estimating an incident severity indicator that corresponds to one or more occupants 14 located within an interior cabin 18 of the vehicle 10, which is involved in a vehicle-related incident. It is to be appreciated that the vehicle 10 may be any type of vehicle such as, but not limited to, a sedan, a truck, sport utility vehicle, van, or motor home. In the non-limiting embodiment as shown in FIG. 1, the vehicle 10 includes one or more controllers 20 in electronic communication with one or more microphones 22, an occupant monitoring system (OMS) 24, a restraint system 26, and a motion-based indicator system 28.

As explained below, the one or more controllers 20 estimate the incident severity indicator corresponding to the occupants 14 located in the vehicle 10, which has undergone a vehicle-related incident, and selects one or more remedial actions based on the incident severity indicator corresponding to the occupants 14. In one embodiment, the vehicle-related incident may refer to a collision between the vehicle 10 and another vehicle located in the surrounding environment, a collision between the vehicle 10 and an object located in the surrounding environment such as, for example, a traffic sign, a roadblock, a tree, or a pole. In another embodiment, the vehicle-related incident may refer to vehicle motion such as, for example, a rollover, sudden braking, a sudden lane change, and sudden swerving. In yet another embodiment, the vehicle-related incident may refer to an incident where one or more of the occupants 14 are experiencing a health emergency such as, for example, fainting or a seizure.

The one or more microphones 22 are positioned within the interior cabin 18 of the vehicle 10 to capture audio signals. In the exemplary embodiment as shown in FIG. 1, the OMS 24 includes one or more cameras 30 positioned within the interior cabin 18 of the vehicle 10 to capture image data indicative of the occupants 14, which indicates a root cause of the vehicle-related incident. It is to be appreciated that the one or more cameras 30 may include red, green, and blue (RGB) cameras that capture visible light image data, infrared cameras that capture infrared image data, or thermal cameras that capture thermal image data. Accordingly, it is to be appreciated that the image data may refer to visible light image data, infrared image data, and thermal image data. It is also to be appreciated that while the present disclosure describes the OMS 24 including one or more cameras 30 capturing image data related to the occupants 14, other types of data may be collected as well. For example, the OMS 24 may include one or more biometric sensors for collecting biometric data and/or one or more radar sensors for detecting a presence and a position of the occupants 14 within the interior cabin 18 of the vehicle 10 as well. The biometric sensors collect biometric data such as, for example, the respiratory rate and the heart rate of the occupants 14.

The restraint system 26 includes one or more restraint-based mechanisms associated with an occupant 14 of the vehicle 10 being activated. In one embodiment, the restraint-based mechanisms may refer to an anchor pretensioner of a seatbelt, a load limiter of the seatbelt, and an airbag associated with an occupant 14. Specifically, as explained below, in an embodiment, the restraint system 26 indicates when an anchor pretensioner is triggered, a load limiter exceeds a corresponding threshold, one or more airbags is deployed, and a stage of deployment of the airbag (e.g., a first stage deployment or a dual stage deployment). The motion-based indicator system 28 includes one or more diagnostic controllers that record motion-based data of the vehicle 10 during the vehicle-related incident. The motion-based data includes, for example, acceleration data and pressure measurements. In embodiments, the motion-based indicator system 28 includes one or more sensing and diagnostic modules (SDM) and/or one or more electronic data recorders (EDM) that record the motion-based data of the vehicle 10. It is to be appreciated that while FIG. 1 illustrates the microphone 22 and sensors for the OMS 24, the restraint system 26, and the motion-based indicator system 28 located within the interior cabin 18, the microphone 22 and the sensors for the OMS 24, the restraint system 26, and the motion-based indicator system 28 may be located along an exterior of the vehicle 10 as well.

Figure 2:
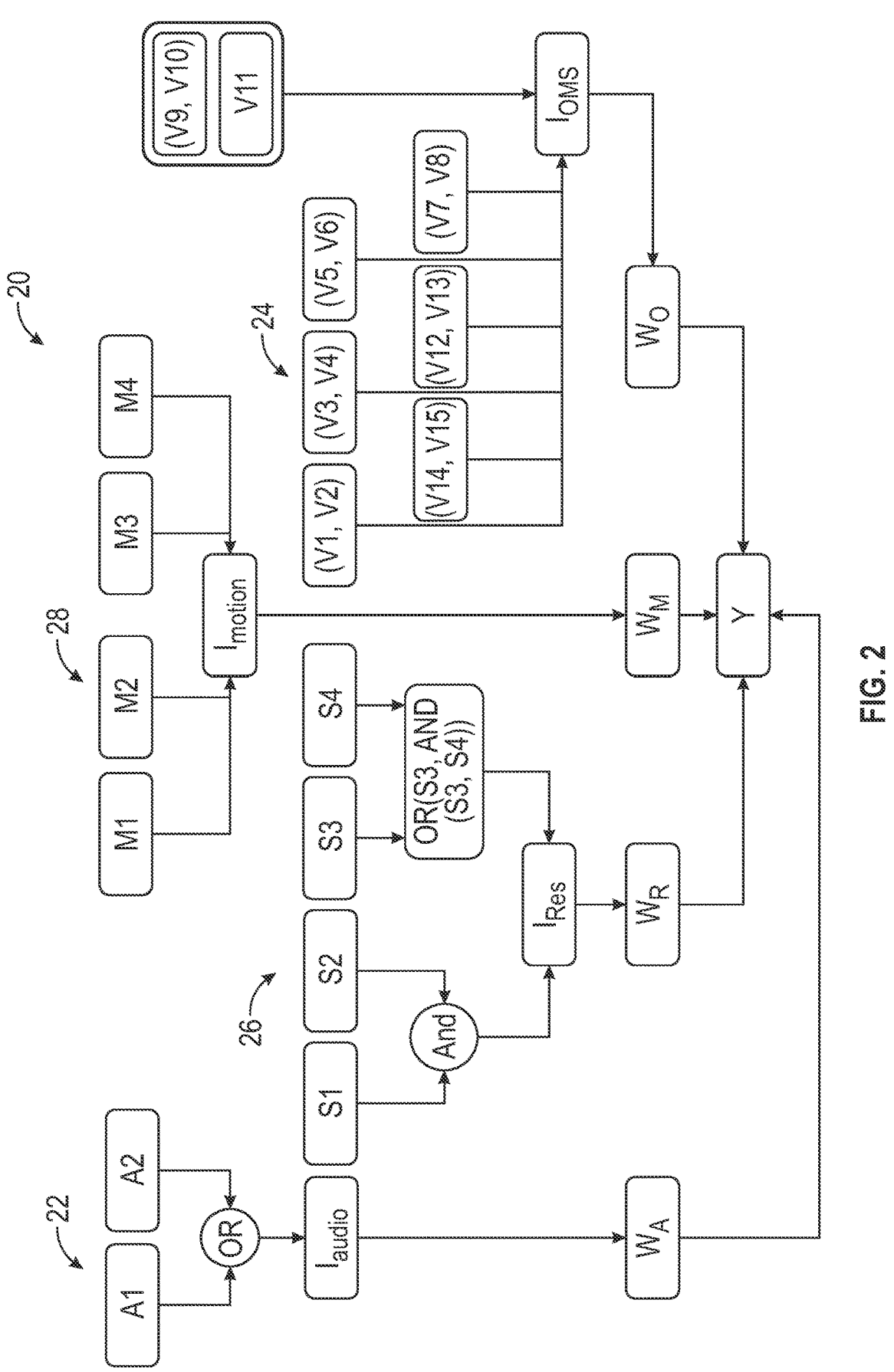
FIG. 2 is a schematic diagram of the one or more controllers receiving input from the microphone, the OMS, the restraint system, and the motion-based indicator system, according to an exemplary embodiment.

FIG. 2 is a schematic diagram illustrating the one or more controllers 20 receiving a plurality of audio-based inputs A1, A2 from the microphone 22, a plurality of scene recognition inputs V1-V15 from the OMS 24, a plurality of restraint-based inputs S1-S4 from the restraint system 26, and a plurality of motion-based inputs M1-M4 from the motion-based indicator system 28. Referring to both FIGS. 1 and 2, the microphone 22 is located within the interior cabin 18 of the vehicle 10 and captures the audio-based inputs A1, A2 indicative of verbal and non-verbal sounds emitted by the occupants 14 of the vehicle 10. The OMS 24 collects the scene recognition inputs V1-V15 that are indicative of a status of the occupants 14. The status of the occupants 14 refers to items such as, for example, an eye status of the occupants 14, which refers to the eyes of an occupant 14 being opened, closed, or blinking, an eye motion input, which refers to motion of the eyes of the occupant 14, and a visual head status input indicates when the head of an occupant 14 is covered by the occupant's hands or another object, such as the airbag, after the vehicle-related incident. In the exemplary embodiment as shown in the figures, the scene recognition inputs are based on the image data captured by the one or more cameras 30.

The restraint system 26 collects a plurality of restraint-based inputs S1-S4 indicative of one or more restraint-based mechanisms associated with an occupant 14 of the vehicle 10 being activated during the vehicle-related incident. The motion-based indicator system 28 collects the plurality of motion-based inputs M1-M4 indicative of the motion of the vehicle 10 during the vehicle-related incident.

As explained below, the one or more controllers 20 combine the plurality of audio-based inputs A1-A2 from the microphone 22 based on at least a 2-value logic system to determine an audio-based indicator $I_{audio}$. In one embodiment, the 2-value logic system refers to either a binary logic system or a ternary logic system. The one or more controllers 20 combine the plurality of scene recognition inputs V1-V15 based on the at least 2-value logic system and a weighted summation, which is described in Equation 1 (which is shown below), to determine an OMS indicator $I_{OMS}$. The one or more controllers 20 combine the plurality of restraint-based inputs S1-S4 from the restraint system 26 based on the at least a 2-value logic system to determine a restraint-based indicator $I_{RES}$. Finally, the one or more controllers 20 combine the plurality of motion-based inputs M1-M4 from the motion-based indicator system 28 based on a weighted sum model to determine a motion-based indicator $I_{motion}$. As also explained below, the one or more controllers 20 fuse together the audio-based indicator $I_{audio}$, the OMS indicator $I_{OMS}$, the restraint-based indicator $I_{RES}$, and the motion-based indicator $I_{motion}$ based on a weighted formula, which is described in Equation 3 (which is shown below), to determine the incident severity indicator Y corresponding to the occupants 14 in the vehicle 10.

The incident severity indicator Y is a numerical value representative of a level of severity of an effect the vehicle-related incident has upon the occupants 14 of the vehicle 10. The effect the vehicle-related incident has upon the occupants 14 of the vehicle 10 refers to a physiological state of the one or more occupants 14, and may indicate conditions such as, for example, the occupant 14 becoming unconscious, going into shock, or experiencing an injury. Merely by way of example, in one embodiment when the incident severity indicator Y ranges in value from greater than or equal to −1.00 to less than or equal to −0.50, this indicates the vehicle 10 did not undergo an vehicle-related incident. When the incident severity indicator Y is greater than or equal to −0.50 and is less than or equal to 0.25, this indicates the level of severity of the effect the vehicle-related incident has upon the occupants 14 is unknown. When the incident severity indicator Y is greater than or equal to 0.25 and is less than or equal to 0.50, this indicates the level of severity of the effect the vehicle-related incident has on the occupants is low. One example of an accident with low severity is when the airbags are not deployed, the occupant 14 is normal and does not generate sounds or eye motion that indicate an accident, and the motion-based indicator system 28 records a higher acceleration than what is normally experienced (e.g., 2 g-force). Finally, when the incident severity indicator Y is greater than or equal to 0.50 and is less than or equal to 1.00, this indicates the level of severity of the effect the vehicle-related incident has upon the occupants 14 is high. One example of an accident with high severity is when the airbags are deployed (both first and second stage), no occupant motion is detected, and the motion-based indicator system 28 records an acceleration of about 30 g-force.

Referring to both FIGS. 1 and 2, in the exemplary embodiment as shown, the audio-based inputs include a speech-based input A1 and a non-speech input A2. The speech-based input A1 represents speech-based sounds generated by the occupants 14 such as, for example, asking for assistance or expressing emotions such as fear, surprise, or shock. The non-speech input A2 represents sounds that are not words generated by the occupants 14 such as crying, moaning, respiration noises, or the sound of the occupant 14 making impact with the interior of the vehicle 10.

Figures 3, 4A:
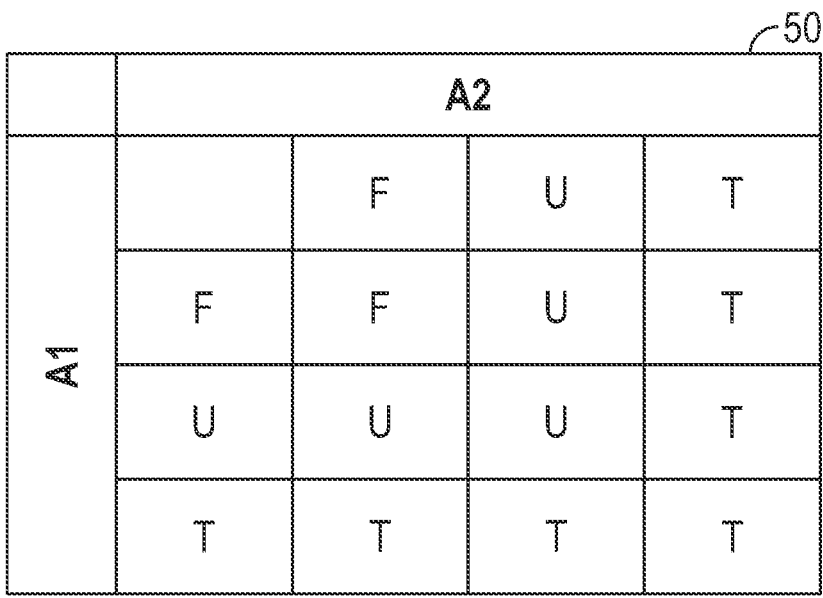
FIG. 3 illustrates a ternary logic OR table for combining two audio-based inputs, according to an exemplary embodiment.
FIGS. 4A-4C illustrate ternary logic tables for combining restraint-based inputs, according to an exemplary embodiment.

In one embodiment, the one or more controllers 20 employ ternary logic to combine the audio-based inputs A1, A2 with one another to determine the audio-based indicator $I_{audio}$. For example, as seen in FIG. 3, a ternary logic OR table 50 is illustrated, where the audio-based inputs are combined based on ternary OR-based logic. The table 50 indicates a truth value of either true, which is indicated by a T, false, which is indicated by a F, and unknown, which is indicated by a U. In the example as shown in FIG. 3, when the truth value is false, this indicates the microphone 22 did not detect any speech-based sounds corresponding to the speech-based input A1. Similarly, the truth value of false also indicates the microphone 22 did not detect any non-speech-based sounds corresponding to the non-speech-based input A2. Similarly, when the truth value is true for the speech-based input A1, this indicates the microphone 22 detected speech-based sounds, and when the truth value is true for the non-speech-based input A2, this also indicates the microphone detected non-speech-based sounds. The unknown truth value indicates no signal was detected by the microphone 22. It is to be appreciated that while the disclosure only illustrates a ternary logic OR table 50 for combining the audio-based inputs A1, A2, a similar logic table may be provided to combine the plurality of scene recognition inputs V1-V15 from the OMS 24 and the plurality of restraint-based inputs S1-S4 from the restraint system 26 as well. It is to be appreciated that while ternary logic is described and is shown in the logic table 50 in FIG. 3, in another embodiment binary logic may be used instead.

Referring to both FIGS. 1 and 2, in the exemplary embodiment as shown, the plurality of scene recognition inputs include eye status inputs V1, V2 based on the eyes of the occupants 14, head status inputs V3, V4 based on the head of the occupants 14, vital status inputs V5, V6, body velocity inputs V7, V8, seat belt status inputs V9, V10, seat belt speed inputs V11, contact inputs V12, V13 indicating contact between the occupants 14 and an interior of the vehicle 10, and airbag inputs V14, V15. Specifically, an eye status input V1 indicates the eye status of the occupants 14, which refers to the eyes of an occupant 14 being opened, closed, or blinking, and an eye motion input V2 indicates motion of the eyes of the occupants 14, such as side-to-side movement, upward and downward movement, and pupil status. In one non-limiting embodiment, the one or more controllers 20 employ a ternary logic AND table to combine the eye status input V1 and the eye motion input V2 with one another to determine a first sub-indicator $O_1$.

A visual head status input V3 indicates when the head of an occupant 14 is covered by the occupant's hands or another object after the vehicle-related incident such as, for example, an airbag that has been deployed. A body motion input V4 indicates head and body motion of the occupants 14, such as side-to-side or upwards and downwards motion of the head. In one non-limiting embodiment, the one or more controllers 20 employ a ternary logic OR table to combine the visual head status input V3 and the body motion input V4 with one another to determine a second sub-indicator $O_2$.

A visual respiration rate input V5 indicates chest movements of the occupants 14 indicating inhaling and exhaling. A skin temperature input V6 indicates the skin temperature and pallor of the occupants 14. In one non-limiting embodiment, the one or more controllers 20 employ a ternary logic OR table to combine the visual respiration rate input V5 and the skin temperature input V6 with one another to determine a third sub-indicator $O_3$.

A head velocity input V7 indicates when the head of the occupants 14 exceed a threshold velocity and a chest velocity input V8 indicates when the chest of the occupants 14 exceed the threshold velocity, where the threshold velocity indicates that an impact severity to the chest of the occupant 14 is severe or high. In one non-limiting embodiment, the one or more controllers 20 employ a ternary logic OR table to combine the head velocity input V7 and the chest velocity input V8 with one another to determine a fourth sub-indicator $O_4$.

A shoulder belt status input V9 indicates when the shoulder belt is not correctly positioned relative to one of the occupants 14 and a lap belt status input V10 indicates when a lap belt is not correctly positioned relative to the occupant 14 because of the vehicle-related incident. In one non-limiting embodiment, the one or more controllers 20 employ a ternary logic OR table to combine the shoulder belt status input V9 and the lap belt status input V10 with one another to determine a fifth sub-indicator $O_5$.

A shoulder belt speed input V11 indicates when the shoulder belt of the occupants 14 exceeds a respective pull-out or payout speed threshold value. A head contact input V12 indicates when the head of the occupant 14 makes hard contact with the interior of the vehicle 10, and a body contact input V13 indicates when a body of an occupant 14 makes hard contact with the interior of the vehicle 10. In one non-limiting embodiment, the one or more controllers 20 employ a ternary logic OR table to combine the head contact input V12 and the body contact input V13 with one another. It is to be appreciated that a sixth sub-indicator $O_6$ is determined based on the shoulder belt speed input V11, the head contact input V12, and the body contact input V13, where the result of the ternary logic OR table for the head contact input V12 and the body contact input V13 is combined with the should belt speed input V11 based on a ternary logic OR table.

An airbag input V14 indicates when an airbag is deployed correctly. An airbag protected input V15 indicates that in the event the airbag deployed correctly, the airbag has protected a given threshold area. In an embodiment, the given threshold area indicates the airbag surface covers the head of the occupant 14. In one non-limiting embodiment, the one or more controllers 20 employ a ternary logic OR table to combine the airbag input V14 and the airbag protected input V15 with one another to determine a seventh sub-indicator $O_7$.

In one embodiment the one or more controllers 20 combine the first sub-indicator $O_1$, the second sub-indicator $O_2$, the third sub-indicator $O_3$, the fourth sub-indicator $O_4$, the fifth sub-indicator $O_5$, the sixth sub-indicator $O_6$, and the seventh sub-indicator $O_7$ together based on a weighted summation to determine the OMS indicator $I_{OMS}$. In one non-limiting embodiment, the weighted summation is expressed in Equation 1 as:

$$I_{OMS} = \sum_{i=1}^{7} \omega_{o_i} \times O_i = 1 \qquad \text{Equation 1}$$

where $\omega$ represents a unique weighting factor for each occupant-based sub-indicator $O_i$. It is to be appreciated that the unique weighting factors $\omega_{o_i}$ are each ranked based on a level of importance, and in embodiments are user-defined values. In another embodiment, the unique weighting factors $\omega_{o_i}$ indicate a degree of certainty quantified as a function of variance.

Referring to FIGS. 1 and 2, in the exemplary embodiment as shown, the plurality of motion-based inputs includes an acceleration and deceleration input M1, an impact angle input M2, a roll-over input M3, and a velocity change input M4. The acceleration and deceleration input M1 indicates an acceleration or a deceleration the vehicle 10 experienced during the vehicle-related incident. The impact angle input M2 indicates an impact angle and an impact direction where the vehicle 10 is impacted during the vehicle-related incident. The roll-over input M3 indicates if the vehicle 10 has experienced roll-over during the vehicle-related incident. Finally, the velocity change input M4 indicates a change in velocity of the vehicle 10 over a time window during the vehicle-related incident.

In one embodiment the one or more controllers 20 combine the acceleration and deceleration input M1, the impact angle input M2, the roll-over input M3, and the velocity change input M4 together based on a weighted sum model to determine the motion-based indicator $I_{motion}$. In one non-limiting embodiment, the weighted sum model is expressed in Equation 2 as:

$$I_{motion} = \omega_{M1} \times M1 + \omega_{M2} \times M2 + \omega_{M3} \times M3 + \omega_{M4} \times M4 \qquad \text{Equation 2}$$

where the weighted sum model includes a unique weighting factor for each motion-based input and are each ranked based on a level of importance. In another embodiment, the weighted sum model includes unique weighting factors for each motion-based input that indicate a degree of certainty quantified as a function of variance. Specifically, $\omega_{M1}$ represents a first weighting factor corresponding to the acceleration and deceleration input M1, $\omega_{M2}$ represents a second weighting factor corresponding to the impact angle input M2, $\omega_{M3}$ represents a third weighting factor corresponding to the roll-over input M3, and $\omega_{M1}$ represents a fourth weighting factor corresponding to the velocity change input M4, where the sum of the first weighting factor, the second weighting factor, the third weighting factor, and the fourth weighting factor is equal to 1.

Referring to both FIGS. 1 and 2, in the exemplary embodiment as shown, the plurality of restraint-based inputs S1-S4 from the restraint system 26 includes an anchor pretensioner input S1, a load limiter input S2, a first stage deployment input S3, and a dual stage deployment input S4. The anchor pretensioner input S1 indicates if the anchor pretensioner corresponding to a seat of one of the occupants 14 is triggered. The load limiter input S2 indicates if the load limiter corresponding to a seat of the occupant 14 exceeds the corresponding threshold. The first stage deployment input S3 indicates if the airbag corresponding to the seat of the occupant 14 has undergone a first stage deployment, and the second stage deployment input S4 indicates if the airbag corresponding to the seat of the occupant 14 has undergone a dual stage deployment.

Figures 4B, 4C:
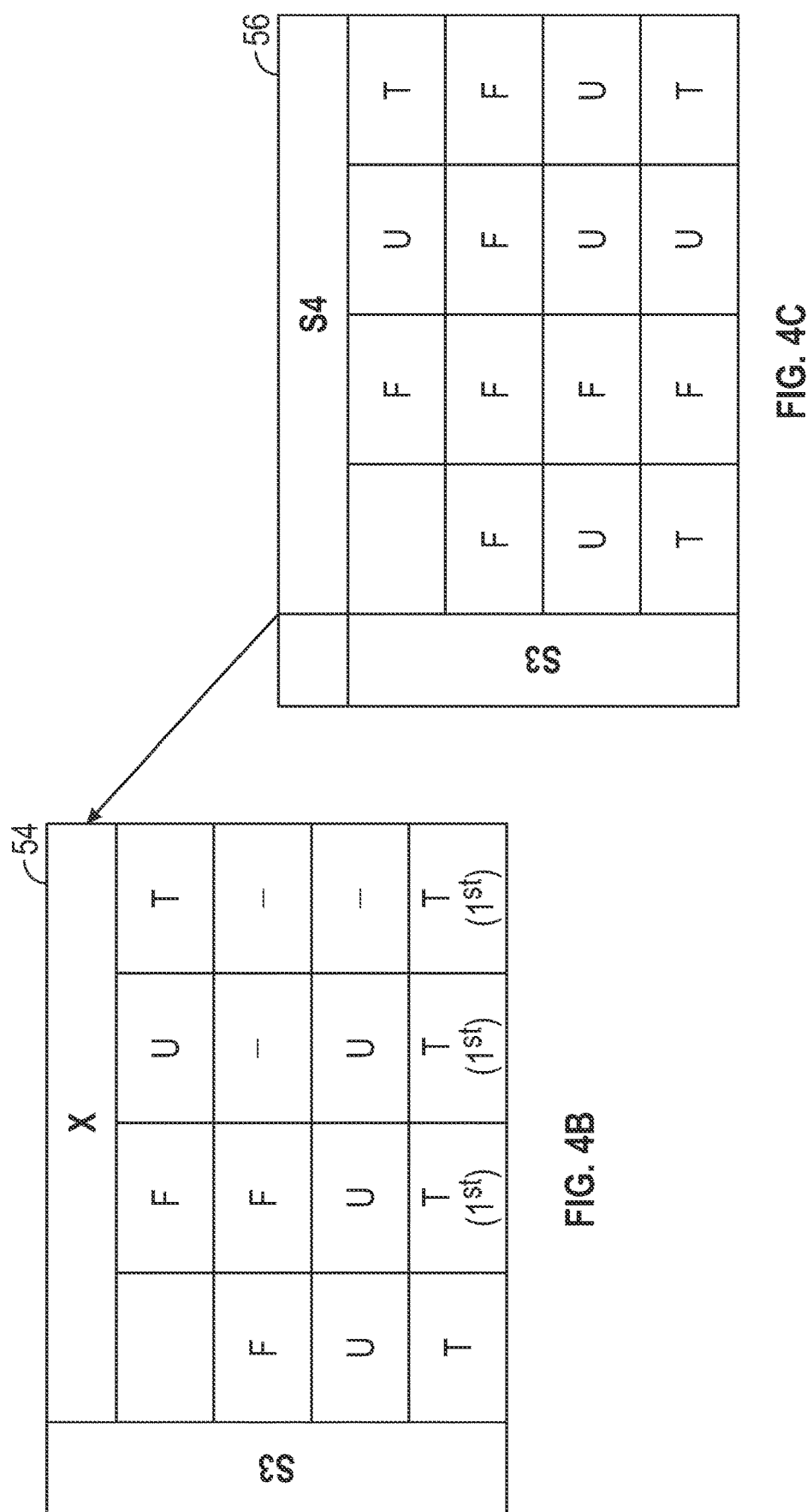

In one embodiment, the one or more controllers 20 employ ternary logic to combine the plurality of restraint-based inputs S1-S4 with one another to determine the restraint-based indicator $I_{Res}$. For example, as seen in FIG. 4A, a ternary logic AND table 52 is illustrated that combine the anchor pretensioner input S1 and the load limiter input S2 together. FIG. 4B illustrates a ternary logic OR table 54 that combines the first stage deployment input S3 with X, where X represents combining the first stage deployment input S3 with the second stage deployment input S4 based on a ternary logic AND table 56, which is illustrated in FIG. 4C.

Referring to FIGS. 1 and 2, the one or more controllers 20 assign a numerical value to the audio-based indicator $I_{audio}$, the OMS indicator Ios, and the restraint-based indicator $I_{RES}$ based on the truth value. Specifically, in an embodiment, the true value corresponds to 1, the unknown value corresponds to 0, and the false value corresponds to −1. The one or more controllers 20 fuse together the audio-based indicator $I_{audio}$, the OMS indicator $I_{OMS}$, and the restraint-based indicator $I_{RES}$, and the motion-based indicator $I_{motion}$ based on the weighted formula to determine the incident severity indicator Y corresponding to the one or more occupants 14. In one embodiment, the weighted formula is expressed in Equation 3 as:

$$Y = W_A I_{audio} + W_M I_{motion} + W_O I_{OMS} + W_R I_{Res} \qquad \text{Equation 3}$$

where $W_A$ is a weight corresponding to the audio-based indicator $I_{audio}$, $W_M$ is a weight corresponding to the motion-based indicator $I_{motion}$, $W_O$ is a weight corresponding to the OMS indicator $I_{OMS}$, and $W_R$ is a weight corresponding to the restraint-based system indicator $I_{Res}$.

It is to be appreciated that a sum of the weights $W_A$, $W_M$, $W_O$, and $W_R$ are equal to 1. In one non-limiting embodiment, the weights $W_A$, $W_M$, $W_O$, and $W_R$ include predefined value. Merely by way of example, in one embodiment the value of the weights $W_A$, $W_M$, $W_O$, and $W_R$ are equal, where each weight has a value of 0.25. In another embodiment, the values for the weights $W_A$, $W_M$, $W_O$, and $W_R$ are adjusted based on a certainty and an importance of the corresponding indicator $I_{audio}$, $I_{OMS}$, $I_{Res}$, and $I_{motion}$. For example, in one embodiment, the values for the weights $W_A$, $W_M$, $W_O$, and $W_R$ are inversely proportional to a corresponding uncertainty value for the corresponding indicator that is quantified based on variance.

Figure 5:
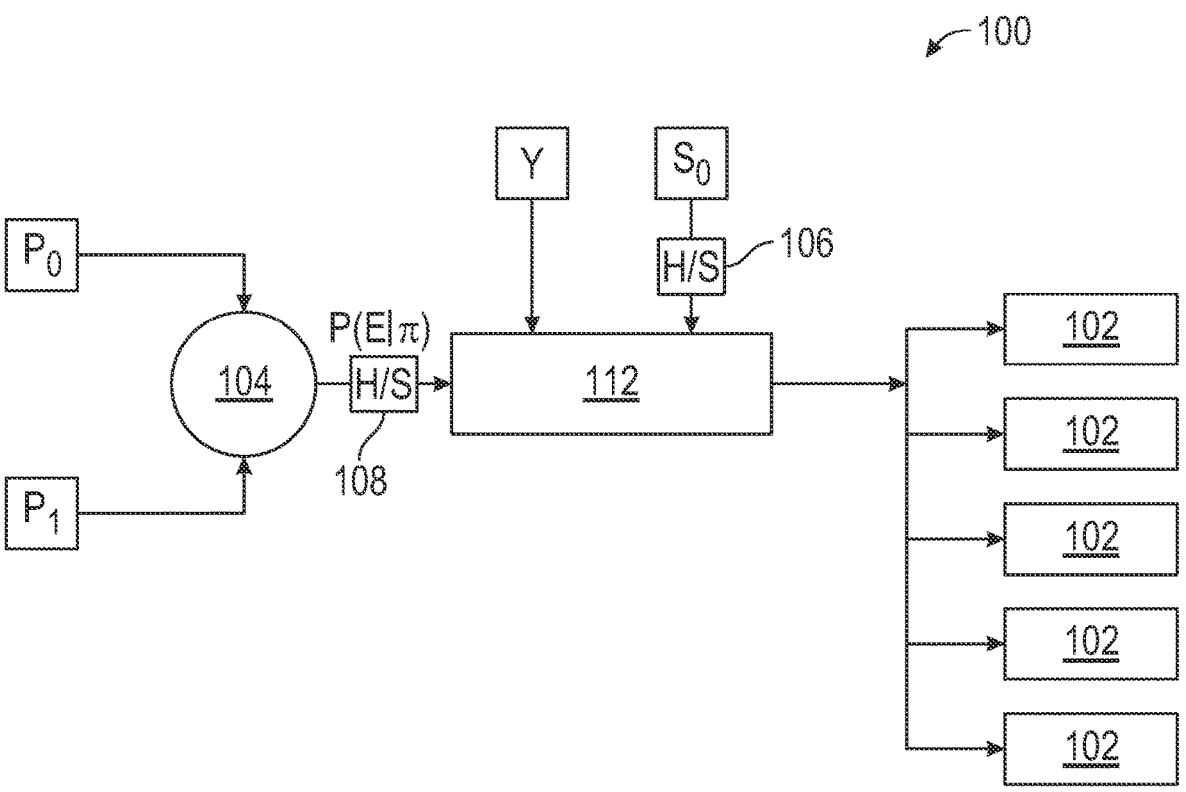
FIG. 5 is a diagram illustrating a cause-action map for selecting the one or remedial actions, according to an exemplary embodiment.

FIG. 5 is a diagram illustrating a cause-action map 100 for selecting the one or remedial actions 102. Referring to both FIGS. 1 and 5, in an embodiment the one or more controllers 20 selects one or more remedial actions 102 by performing cause-action mapping based on the incident severity indicator Y corresponding to the one or more occupants 14, an unconsciousness indicator $S_0$, and a root cause probability indicator P(E|π). The one or more remedial actions 102 represent activities that assist the one or more occupants 14 of the vehicle 10 after the vehicle-related incident. Some examples of the remedial actions 102 include, but are not limited to, contacting emergency personnel, unlocking the doors of the vehicle 10, lowering the windows of the vehicle 10, sending an SOS signal to one or more vehicles that are located within a predefined radius from the vehicle 10, and contacting non-emergency personnel.

The unconsciousness probability indicator $S_0$ indicates the occupants 14 are unconscious and ranges in value from 0 to 1. In one non-limiting embodiment, the one or more controllers 20 determine the occupants 14 are unconscious when the unconsciousness indicator $S_0$ is equal to or greater than 0.5. The root cause probability indicator P(E|π) indicates a probability that of a potential root cause of the vehicle-related incident is true. The cause-action map 100 shown in FIG. 5 includes a hard/soft thresholding block 106 corresponding to the unconsciousness indicator $S_0$ and a hard/soft thresholding block 108 corresponding to the root cause probability indicator P(E|π). In the non-limiting embodiment as shown in FIG. 5, the root cause probability indicator P(E|π) is based on a collision-based probability $P_0$ and a motion-based probability $P_1$. The collision-based probability $P_0$ indicates a probability the root cause of the vehicle-related incident is because the vehicle 10 was involved in a collision. The cause-action map 100 also includes a cause-action mapping block 112 that receives the unconsciousness indicator $S_0$, the root cause probability indicator P(E|π), and the incident severity indicator Y corresponding to the one or more occupants 14 and performs cause-action mapping to determine the root cause of the vehicle-related incident.

The motion-based probability $P_1$ indicates a probability the root cause of the vehicle-related incident is motion-based behavior such as, for example, such as a rollover, sudden braking, a sudden lane change, and sudden swerving. The collision-based probability $P_0$ and the motion-based probability $P_1$ are combined in a noisy OR-model 104. In one embodiment, the root cause probability indicator P(E|π) is determined based on Equation 4 as:

$$Prob(E_1 \mid \pi: \text{range over all parents of } E) = \prod\nolimits_{\pi_{i \in s}} P_i \qquad \text{Equation 4}$$

where S presents the set of parents that are true (on) and $\pi_i$ includes a range that includes all parents of the expected value E, and $Prob(E_0|\pi)=1-Prob(E_1|\pi)=1-P_1.P_2, \ldots,$ $P_n=1-[(1-Q_1)(1-Q_2) \ldots (1-Q_n)]$, $P_i+Q_i=1(\forall i)$, $E_1+E_0=1$, where n=2 (e.g., $P_1$, $P_2$) and in the present example and represents the number of potential root causes.

In one non-limiting embodiment, the one or more controllers 20 determine the root cause is true when the root cause probability indicator P(E|π) is equal to or greater than 0.5. As an example, when the incident severity indicator Y indicates the level of severity of the effect the vehicle-related incident has upon the occupants 14 is high, the unconsciousness probability indicator $S_0$ indicates the occupants 14 are unconscious, and the root cause probability indicator P(E|π) indicates the root cause is not true, the one or more controllers 20 select contacting emergency personnel, unlocking the doors of the vehicle 10, sending an SOS signal to one or more vehicles that are located within the predefined radius from the vehicle 10, and contacting non-emergency personnel as the remedial actions 102.

Referring generally to the figures, the disclosed severity estimation system provides various technical effects and benefits. Specifically, the severity estimation system employs a multi-modal approach for estimating the incident severity indicator corresponding to one or more occupants located within an interior cabin of a vehicle involved in a vehicle-related incident, which indicates a level of severity of the effect the vehicle-related incident has upon the occupants. The incident severity indicator may be used to select one or more remedial actions that aid the occupants after the vehicle-related incident has occurred. In other words, the disclosed severity estimation system selects remedial actions based on the severity of the effect the vehicle-related incident has on the occupants, which may result in more appropriate or helpful actions being performed to assist the occupants after a vehicle-related incident.

The controllers may refer to, or be part of an electronic circuit, a combinational logic circuit, a field programmable gate array (FPGA), a processor (shared, dedicated, or group) that executes code, or a combination of some or all of the above, such as in a system-on-chip. Additionally, the controllers may be microprocessor-based such as a computer having a at least one processor, memory (RAM and/or ROM), and associated input and output buses. The processor may operate under the control of an operating system that resides in memory. The operating system may manage computer resources so that computer program code embodied as one or more computer software applications, such as an application residing in memory, may have instructions executed by the processor. In an alternative embodiment, the processor may execute the application directly, in which case the operating system may be omitted.

The description of the present disclosure is merely exemplary in nature and variations that do not depart from the gist of the present disclosure are intended to be within the scope of the present disclosure. Such variations are not to be regarded as a departure from the spirit and scope of the present disclosure.

What is claimed is:

1. A severity estimation system for one or more occupants located in an interior cabin of a vehicle involved in a vehicle-related incident, the severity estimation system comprising:

one or more microphones located within the interior cabin of the vehicle that capture a plurality of audio-based inputs indicative of verbal and non-verbal sounds emitted by the one or more occupants of the vehicle;

an occupant monitoring system (OMS) that collects a plurality of scene recognition inputs indicative of a status of the occupants;

a restraint system that collects a plurality of restraint-based inputs indicative of one or more restraint-based mechanisms associated with an occupant of the vehicle being activated during the vehicle-related incident, wherein the one or more restraint-based mechanisms refer to one or more of the following: an anchor pretensioner of a seatbelt, a load limiter of the seatbelt, and an airbag;

a motion-based indicator system that collects a plurality of motion-based inputs indicative of the motion of the vehicle during the vehicle-related incident; and one or more controllers in electronic communication with the one or more microphones, the OMS, the restraint system, and the motion-based indicator system, the one or more controllers executing instructions to:

combine the plurality of audio-based inputs based on at least a 2-value logic system to determine an audio-based indicator, the plurality of scene recognition inputs based on the at least 2-value logic system to determine an OMS indicator, and the plurality of restraint-based inputs based on the at least 2-value logic system to determine a restraint-based indicator;

combine the plurality of motion-based inputs from the motion-based indicator system based on a weighted sum model to determine a motion-based indicator;

fuse together the audio-based indicator, the OMS indicator, the restraint- based indicator, and the motion-based indicator to determine an incident severity indicator corresponding to the one or more occupants, wherein the incident severity indicator is a numerical value representative of a level of severity of an effect the vehicle-related incident has upon the one or more occupants; and select one or more remedial actions in real-time based on the incident severity indicator, an unconsciousness probability indicator, and a root cause probability indicator; and instruct the vehicle to execute the one or more remedial actions.

2. The severity estimation system of claim 1, wherein the one or more controllers execute instructions to fuse together the audio-based indicator, the OMS indicator, the restraint-based indicator, and the motion-based indicator based on a weighted formula to determine the incident severity indicator.

3. The severity estimation system of claim 2, wherein the weighted formula is expressed as:

$$Y = W_A I_{audio} + W_M I_{motion} + W_O I_{OMS} + W_R I_{Res}$$

wherein $W_A$ is a weight corresponding to the audio-based indicator $I_{audio}$, $W_M$ is a weight corresponding to the motion-based indicator $I_{motion}$, $W_O$ is a weight corresponding to the OMS indicator $I_{OMS}$, and $W_R$ is a weight corresponding to the restraint-based indicator $I_{Res}$.

4. The severity estimation system of claim 1, wherein the one or more remedial actions include one or more of the following: contacting emergency personnel, unlocking doors of the vehicle, lowering windows of the vehicle, sending an SOS signal to one or more vehicles that are located within a predefined radius from the vehicle, and contacting non-emergency personnel.

5. The severity estimation system of claim 1, wherein the 2-value logic system is one of a binary logic system and a ternary logic system.

6. The severity estimation system of claim 1, wherein the audio-based inputs are combined based on ternary OR-based logic.

7. The severity estimation system of claim 1, wherein the OMS includes one or more cameras positioned within the interior cabin of the vehicle to capture image data indicative of the one or more occupants.

8. The severity estimation system of claim 7, wherein the one or more cameras include one or more of the following: a red, green, and blue (RGB) camera that captures visible light image data, an infrared camera that captures infrared image data, and a thermal camera that captures thermal image data.

9. The severity estimation system of claim 1, wherein the OMS includes one or more of the following: one or more biometric sensors and one or more radar sensors.

10. The severity estimation system of claim 1, wherein the plurality of scene recognition inputs includes one or more of the following: eye status inputs based on the eyes of the occupants, head status inputs based on the head of the occupants, vital status inputs, body velocity inputs, seat belt status inputs, seat belt speed inputs, contact inputs indicating contact between the occupants and an interior of the vehicle, and airbag inputs.

11. The severity estimation system of claim 1, wherein the plurality of motion-based inputs includes one or more of the following: an acceleration and deceleration input, an impact angle input, a roll-over input, and a velocity change input.

12. The severity estimation system of claim 11, wherein the weighted sum model is expressed as:

$$I_{motion} = \omega_{M1} \times M1 + \omega_{M2} \times M2 + \omega_{M3} \times M3 + \omega_{M4} \times M4 = 1$$

15 wherein "$\omega_{M1}$" represents a first weighting factor corresponding to the acceleration and deceleration input M1, "$\omega_{M2}$," represents a second weighting factor corresponding to the impact angle input M2, "$\omega_{M3}$" represents a third weighting factor corresponding to the roll-over input M3, and "$\omega_{M1}$" represents a fourth weighting factor corresponding to the velocity change input M4.

13. The severity estimation system of claim 1, wherein the plurality of restraint-based inputs from the restraint system include one or more of the following: an anchor pretensioner input, a load limiter input, a first stage deployment input, and a dual stage deployment input.

14. The severity estimation system of claim 1, wherein the motion-based indicator system includes one or more of the following: a sensing and diagnostic module (SDM) and an electronic data recorder (EDM).

15. A severity estimation system for one or more occupants located in an interior cabin of a vehicle involved in a vehicle-related incident, the severity estimation system comprising:
    one or more microphones located within the interior cabin of the vehicle that capture a plurality of audio-based inputs indicative of verbal and non-verbal sounds emitted by the one or more occupants of the vehicle;
    an OMS that collects a plurality of scene recognition inputs indicative of a status of the occupants;
    a restraint system that collects a plurality of restraint-based inputs indicative of one or more restraint-based mechanisms associated with an occupant of the vehicle being activated during the vehicle-related incident, wherein the one or more restraint-based mechanisms refer to one or more of the following: an anchor pretensioner of a seatbelt, a load limiter of the seatbelt, and an airbag;
    a motion-based indicator system that collects a plurality of motion-based inputs indicative of the motion of the vehicle during the vehicle-related incident; and
    one or more controllers in electronic communication with the one or more microphones, the OMS, the restraint system, and the motion-based indicator system, the one or more controllers executing instructions to:
        combine the plurality of audio-based inputs based on at least a 2-value logic system to determine an audio-based indicator, the plurality of scene recognition inputs based on the at least 2-value logic system to determine an OMS indicator, and the plurality of restraint-based inputs based on the at least 2-value logic system to determine a restraint-based indicator;
        combine the plurality of motion-based inputs from the motion-based indicator system based on a weighted sum model to determine a motion-based indicator;
        fuse together the audio-based indicator, the OMS indicator, the restraint-based indicator, and the motion-based indicator based on a weighted formula to determine an incident severity indicator corresponding to the one or more occupants, wherein the incident severity indicator is a numerical value representative of a level of severity of an effect the vehicle-related incident has upon the one or more occupants;
        select one or more remedial actions in real-time based on the incident severity indicator, an unconsciousness probability indicator, and a root cause probability indicator; and
        instruct the vehicle to execute the one or more remedial actions.

16

16. The severity estimation system of claim 15, wherein the weighted formula is expressed as:

$$Y = W_A I_{audio} + W_M I_{motion} + W_O I_{OMS} + W_R I_{Res}$$

wherein $W_A$ is a weight corresponding to the audio-based indicator $I_{audio}$, $W_M$ is a weight corresponding to the motion-based indicator $I_{motion}$, $W_O$ is a weight corresponding to the OMS indicator $I_{OMS}$, and $W_R$ is a weight corresponding to the restraint-based indicator $I_{RES}$.

17. The severity estimation system of claim 15, wherein the one or more remedial actions include one or more of the following: contacting emergency personnel, unlocking doors of the vehicle, lowering windows of the vehicle, sending an SOS signal to one or more vehicles that are located within a predefined radius from the vehicle, and contacting non-emergency personnel.

18. A severity estimation system for one or more occupants located in an interior cabin of a vehicle involved in a vehicle-related incident, the severity estimation system comprising:
    one or more microphones located within the interior cabin of the vehicle that capture a plurality of audio-based inputs indicative of verbal and non-verbal sounds emitted by the one or more occupants of the vehicle;
    an OMS that collects a plurality of scene recognition inputs indicative of a status of the occupants;
    a restraint system that collects a plurality of restraint-based inputs indicative of one or more restraint-based mechanisms associated with an occupant of the vehicle being activated during the vehicle-related incident, wherein the one or more restraint-based mechanisms refer to one or more of the following: an anchor pretensioner of a seatbelt, a load limiter of the seatbelt, and an airbag;
    a motion-based indicator system that collects a plurality of motion-based inputs indicative of the motion of the vehicle during the vehicle-related incident; and
    one or more controllers in electronic communication with the one or more microphones, the OMS, the restraint system, and the motion-based indicator system, the one or more controllers executing instructions to:
        combine the plurality of audio-based inputs based on at least a 2-value logic system to determine an audio-based indicator, the plurality of scene recognition inputs based on the at least 2-value logic system to determine an OMS indicator, and the plurality of restraint-based inputs based on the at least 2-value logic system to determine a restraint-based indicator;
        combine the plurality of motion-based inputs from the motion-based indicator system based on a weighted sum model to determine a motion-based indicator;
        fuse together the audio-based indicator, the OMS indicator, the restraint-based indicator, and the motion-based indicator based on a weighted formula to determine an incident severity indicator corresponding to the one or more occupants, wherein the incident severity indicator is a numerical value representative of a level of severity of an effect the vehicle-related incident has upon the one or more occupants;
        select one or more remedial actions based on the incident severity indicator, an unconsciousness probability indicator, and a root cause probability indicator; and instruct the vehicle to execute the one or more remedial
actions.

\* \* \* \* \*